United States Patent [19]
Pietruszkiewicz et al.

[11] Patent Number: 4,731,470
[45] Date of Patent: Mar. 15, 1988

[54] [(5,6-DICHLORO-3-OXO-2,9A-ALKANO-2,3,9,9A-TETRAHYDRO-1H-FLUOREN-7-YL)OXY]ALKANOIC ACIDS AND ALKANIMIDAMIDES

[75] Inventors: Adolph M. Pietruszkiewicz, North Wales; Otto W. Woltersdorf, Jr., Chalfont; Edward J. Cragoe, Jr., Lansdale, all of Pa.

[73] Assignee: Merck & Co., Inc., Rahway, N.J.

[21] Appl. No.: 926,161

[22] Filed: Nov. 3, 1986

[51] Int. Cl.$^4$ .............................................. C07C 69/94
[52] U.S. Cl. ...................................... 562/461; 560/53; 564/226; 564/247; 564/225; 546/204; 548/353; 548/569; 544/294

[58] Field of Search .......................... 562/461; 560/53; 564/226, 247, 225, 226; 546/204; 548/353, 569; 544/294; 514/325, 398, 399, 428, 545, 509, 256, 294

[56] References Cited

U.S. PATENT DOCUMENTS

| 4,316,043 | 2/1982 | Cragoe et al. | 560/53 |
| 4,317,922 | 3/1982 | Cragoe et al. | 562/461 |
| 4,337,354 | 6/1982 | Cragoe et al. | 562/461 |
| 4,356,313 | 10/1982 | Cragoe et al. | 560/53 |
| 4,356,314 | 10/1982 | Cragoe et al. | 560/53 |

OTHER PUBLICATIONS

"Agents for the Treatment of Brain Injury", J. Med. Chem., (1982), 25, 567–579—Cragoe, et al.
"Agents for the Treatment of Brain Edema", J. Med. Chem., (1986) 29, 825–841—Cragoe, et al.

Primary Examiner—Paul J. Killos
Attorney, Agent, or Firm—Charles M. Caruso; Hesna J. Pfeiffer

[57] ABSTRACT

The invention relates to novel [(5,6-dichloro-3-oxo-2,9a-alkano--2,3,9,9a-tetrahydro-1H-fluoren-7-yl)oxy]alkanoic acids and alkanimidamides, their derivatives, and their salts. The compounds are useful for the treatment and prevention of injury to the brain and of edema due to head trauma, stroke (particularly ischemic), arrested breathing, cardiac arrest, Reye's syndrome, cerebral thrombosis, cerebral embolism, cerebral hemorrhage, cerebral tumors, encephalomyelitis, spinal cord injury, hydrocephalus, post-operative brain injury trauma, edema due to cerebral infections including that due to AIDS virus, various brain concussions and elevated intracranial pressure.

19 Claims, No Drawings

[(5,6-DICHLORO-3-OXO-2,9A-ALKANO-2,3,9,9A-TETRAHYDRO-1H-FLUOREN-7-YL)OXY]ALKANOIC ACIDS AND ALKANIMIDAMIDES

BACKGROUND OF THE INVENTION

Trauma to the brain or spinal cord caused by physical forces acting on the skull or spinal column, by ischemic stroke, arrested breathing, cardiac arrest, Reye's syndrome, cerebral thrombosis, cerebral embolism, cerebral hemorrhage, encephalomyelitis, hydrocephalus, post-operative brain injury, cerebral infections, AIDS virus, various concussions and elevated intracranial pressure results in edema and swelling of the affected tissues. This is followed by ischemia, hypoxia, necrosis, temporary or permanent brain and/or spinal cord injury and may result in death. The tissue mainly affected are classified as grey matter, more specifically astroglial cells. The specific therapy currently used for the treatment of the medical problems described include various kinds of diuretics (particularly osmotic diuretics), steroids (such as, 6-α-methylprednisolone succinate) and barbiturates. The usefulness of these agents is questionable and they are associated with a variety of untoward complications and side effects. Thus, the compounds of this invention comprise a novel and specific treatment of medical problems where no specific therapy is available.

Two recent publications, one entitled "Agents for the Treatment of Brain Injury" 1. (Aryloxy)alkanoic Acids, Cragoe et al, J. Med. Chem., (1982) 25, 567–79, and the other entitled "Agents for the Treatment of Brain Edema: 2 [(2,3,9,9a-tetrahydro-3-oxo-9a-substituted-1H-fluoren-7-yl)oxy]alkanoic Acids and Some of Their Analogs", Cragoe et al., J. Med. Chem. (1986), 29, 825–841, report on recent experimental testing of agents for treatment of brain injury and review the current status of treatment of brain injury. Additionally, U.S. Pat. Nos. 4,316,043, 4,317,922, 4,337,354, 4,356,313 and 4,356,314 disclose certain alkanoic and cycloalkanoic acids for the treatment of grey matter edema.

The compounds of the invention have the added advantage of being devoid of the pharmacodynamic, toxic or various side effects characteristic of the diuretics, steroids and barbiturates.

DESCRIPTION OF THE INVENTION

The compounds of the instant invention are best characterized by reference to the following structural Formula (I):

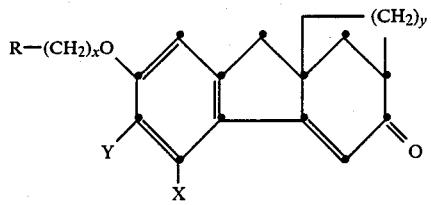

wherein:
R is —COOR$^1$,

R$^1$ is hydrogen, C$_1$-C$_6$ alkyl, C$_1$-C$_6$ alkylcarboxy such as 1-carboxy-1-methylethyl;

R$^2$ is NH$_2$, NHR$^4$ or NR$^4$R$^5$;

R$^3$ is NH or NR$^4$;

R$^4$, R$^5$ are each independently lower alkyl, branched or unbranched, containing from 1 to 5 carbon atoms, or amino, provided that R$^4$ and R$^5$ are not both amino;

wherein R$^2$ and R$^3$ may be joined together via R$^4$ to form a heterocyclic ring of 5 or 6 atoms containing 2 nitrogen atoms and 3 or 4 carbon atoms, such as:

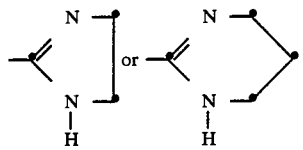

or wherein R$^4$ and R$^5$ may be joined together to form a 5- or 6-membered ring containing one nitrogen atom and 4 or 5 carbon atoms, such as:

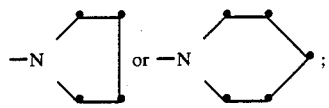

X and Y are halo or lower alkyl, such as methyl; and x is 1 to 4; y is 1 to 3.

Since both the 2- and the 9a-carbon atoms are asymmetric, the compounds of the invention could consist of two diastereomers each composed of a racemate consisting of two enantiomers. However, the steric constraints of the final annulation lead to the formation of primarily only one racemate. These racemates of their precursors can be resolved so that pure enantiomers can be prepared, thus the invention includes the pure enantiomers. This is an important point since some of the racemates consist of one enantiomer which is much more active than the other one. Furthermore, the less active enantiomer generally possesses the same intrinsic toxicity as the more active enantiomer. In addition, it can be demonstrated that the less active enantiomer depresses the inhibitory action of the active enantiomer at the tissue level. Thus, for three reasons it is advantageous to use the pure, more active enantiomer rather than the racemate.

Since the alkanoic acid products of the invention are acidic, the invention also includes the obvious pharmaceutically acceptable salts such as the sodium, potassium, ammonium, trimethylammonium, piperazinium, 1-methylpiperazinium, guanidinium, bis-(2-hydroxyethyl)ammonium, N-methyl-glucosammonium and the like salts.

Likewise, the ethanimidamide products of the invention are basic, the invention also includes the obvious pharmaceutically acceptable acid addition salts such as the hydrochloride, hydrobromide, sulfate, isethionate, acetate, methanesulfonate, maleate, succinate and the like salts.

It is also to be noted that the compounds of Formula I, as well as their salts, often form solvates with the solvents in which they are prepared or from which they are recrystallized. These solvates may be used per se or they may be desolvated by heating (e.g. at 70° C.) in vacuo.

Although the invention primarily involves novel [(5,6-dichloro-3-oxo-2,9a-alkano-2,3,9,9a-tetrahydro-1H-fluoren-7-yl)oxy]-alkanoic acids and alkanimidamides, and their salts, it also includes their derivatives, such as amides, esters, oximes, hydrazones and the like. Additionally, this invention includes pharmaceutical compositions in unit dosage form containing a pharmaceutical carrier and an effective amount of a compound of Formula I, its R or S enantiomer, or the pharmaceutically acceptable salts thereof, for treating brain injury. The method of treating a person with brain injury by administering said compounds or said pharmaceutical compositions is also a part of this invention.

PREFERRED EMBODIMENT OF THE INVENTION

The preferred embodiments of the instant invention are realized in structural Formula II

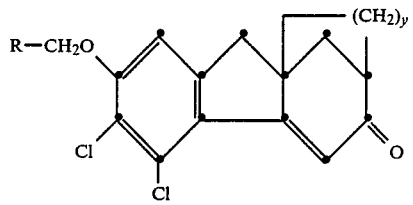

(II)

wherein:
R is —COOH, —COOC(CH₃)₂COOH or

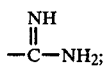

and y is 1 or 2.

Also included are the enantiomers of each racemate.

A preferred compound is [(5,6-dichloro-2,9a-ethano-3-oxo-2,3,9,9a-tetrahydro-1H-fluoren-7-yl)oxy]acetic acid.

Also preferred is [(5,6-dichloro-3-oxo-2,9a-propano-2,3,9,9a-tetrahydro-1H-fluoren-7-yl)oxy]acetic acid.

Also preferred is 1-carboxy-1-methylethyl [(5,6-dichloro-2,9a-ethano-3-oxo-2,3,9,9a-tetrahydro-1H-fluoren-7-yl)oxy]acetate.

Also preferred is 2-[(5,6-dichloro-2,9a-ethano-3-oxo-2,3,9,9a-tetrahydro-1H-fluoren-7-yl)oxy]-ethanimidamide hydrochloride.

Also preferred is [(5,6-dichloro-3-oxo-2,9a-propano-2,3,9,9a-tetrahydro-1H-fluoren-7-yl)oxy]ethanimidamide hydrochloride.

Especially preferred are the pure enantiomers since, in most instances, one enantiomer is more active biologically then its antipode.

Included within the scope of this invention are the pharmaceutically acceptable salts of [(5,6-dichloro-3-oxo-2,9a-alkano-2,3,9,9a-tetrahydro-1H-fluoren-7-yl)oxy]alkanoic acids and alkanimidamides, since a major medical use of these compounds is solutions of their soluble salts which can be administered parenterally.

Thus, the acid addition salts of the carboxylic acids can be prepared by the reaction of the [(5,6-dichloro-3-oxo-2,9a-alkano-2,3,9,9a-tetrahydro-1H-fluoren-7-yl)oxy]alkanoic acids, of this invention with an appropriate alkali metal hydroxide, carbonate or bicarbonate such as sodium hydroxide, potassium hydroxide, sodium carbonate, sodium bicarbonate and the like or an organic base, such as ammonium hydroxide, piperazine, 1-methylpiperazine, guanidine, bis-(2-hydroxyethyl)amine, N-methylglucosamine and the like salts. The salts of the alkanimidamides of this invention may be prepared by reaction with an appropriate pharmaceutically acceptable mineral acid or organic carboxylic acid, such as hydrochloric acid, sulfuric acid, hydrobromic acid, isethionic acid, methanesulfonic acid, maleic acid, succinic acid, acetic acid and the like. The salts selected are derived from among the non-toxic, pharmaceutically acceptable acids.

The synthesis of the compounds of Formula I of this invention is accomplished by the following procedures illustrated by the synthesis of Formula Ia, Ib, Ic and Ie.

The compound of Formula I wherein x=1, y=2, X=Y=Cl and R=COOH (Formula Ia) is prepared by the following 8-step synthesis: 2,3-Dichloroanisole (III) is reacted under Friedel-Crafts conditions with 5-chloropentanoyl chloride in the presence of aluminum chloride using methylene chloride as a solvent. The reagents are united at 0°–5° C. and then allowed to stir at ambient temperature for 10–20 hours. Quenching the reaction mixture in ice produces the desired ketone of Formula (IV).

The reaction of the compound of Formula IV with N,N,N'N'-tetramethyldiaminomethane and acetic anhydride at 50° C. followed by heating at 100° for 1.5–3 hours and 12–20 hours at ambient temperature yields the compound of Formula V upon quenching in ice and basification with sodium hydroxide.

Cyclization of the compound of Formula V to form the compound of Formula VI is accomplished by treatment with concentrated sulfuric acid at 20° to 40° for 2 to 4 hours followed by quenching in ice.

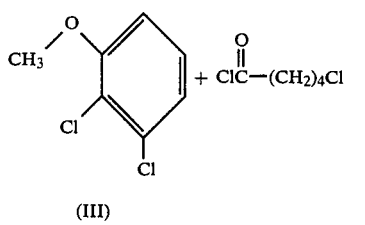

(III)

Step A →

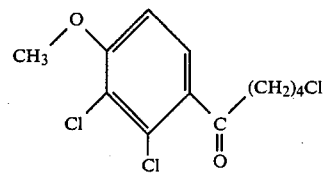

(IV)

Step B  1. (CH₃)₂NCH₂N(CH₃)₂
        2. DMF

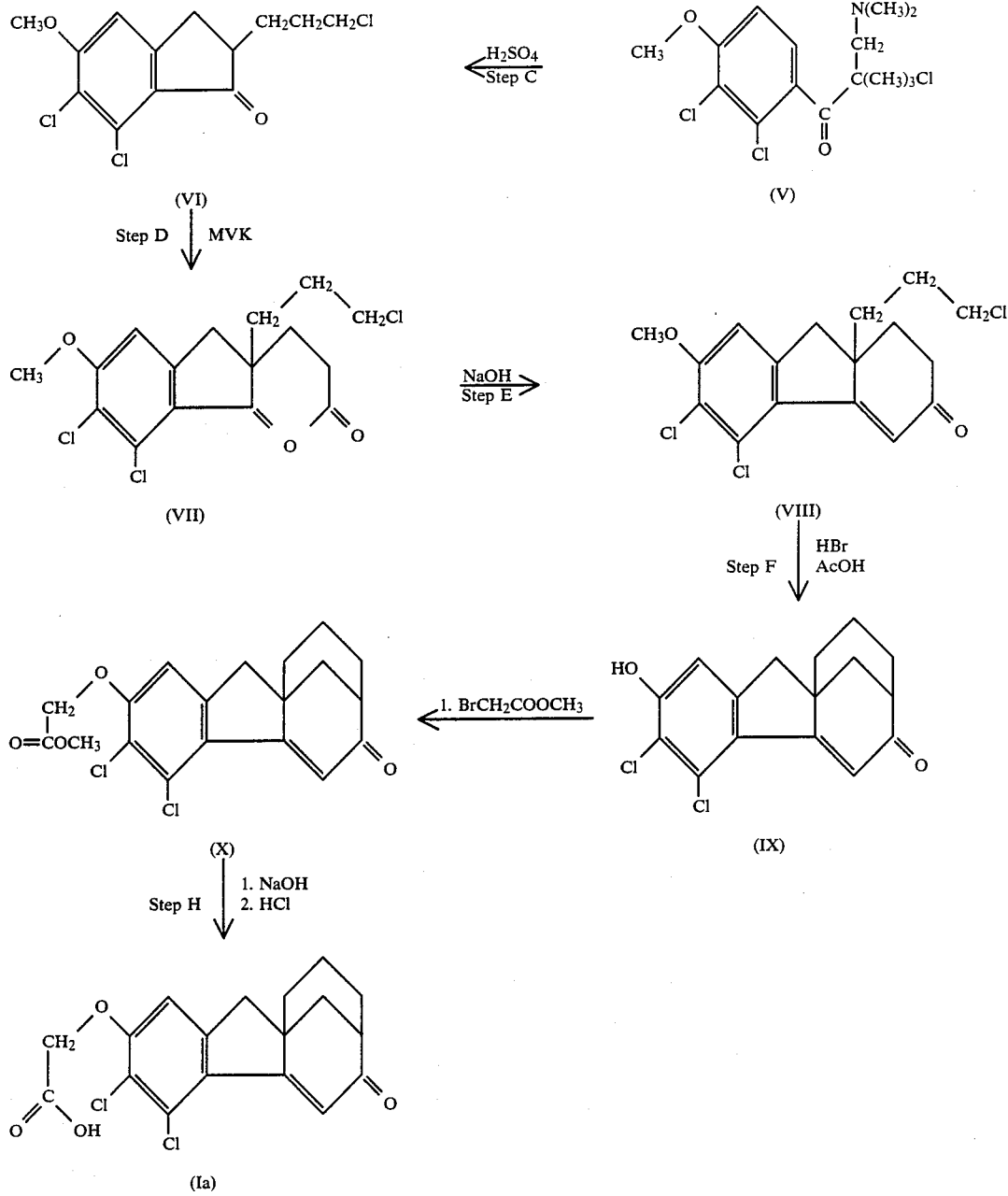

The reaction of the compound of Formula VI with methyl vinyl ketone (MVK) in a solvent such as tetrahydrofuran and a catalytic amount of a base such as 1,5-diazabicyclo[4.3.0]non-5-ene (DBN) or benzyltrimethylammonium hydroxide at ambient temperature for 1 to 5 hours gave the diketone of Formula VII.

Cyclization of the compound of Formula VII to the 1,2,9,9a-tetrahydrofluoren-3-one of Formula VIII is accomplished by refluxing for 1.5 to 3 hours with aqueous methanolic sodium hydroxide solution.

Refluxing a solution of the compound of Formula VIII in a mixture of water and acetic acid and containing about 40% hydrobromic acid for 5 to 10 hours produced both the cleavage of the ether and cyclization to yield the phenol of Formula IX.

Reaction of the compound of Formula IX with methyl bromoacetate in a solvent, such as N,N-dimethylformamide containing potassium carbonate and heating at 50° to 70° C. for 4 to 6 hours gave the ester of Formula X.

Saponification of the ester of Formula X was accomplished by heating an aqueous methanolic solution of sodium hydroxide on a steam bath for 45 minutes to 1¼ hours followed by cooling and acidification with hydrochloric acid to produce the compound of Formula Ia.

The ten-step synthesis of the compound of Formula I wherein x=1, y=1, x=y=Cl and R=COOH (i.e., Formula Ib) is shown in the reaction sequence of the compound of Formula XI to the compound of Formula Ib. A Friedel-Crafts reaction involving the compound of Formula XI and 4-chlorobutyryl chloride (Formula XII) gave the ketone of Formula XIII. The reaction is conducted in a solvent such as methylene chloride at a temperature in the range of 20° to 40° C. for a period of 2.5 to 5 hours gives the desired compound upon quenching in ice.
The α-methylene derivative of Compound XIII (i.e., compound XIV) is prepared by the reaction of the compound of Formula XIII
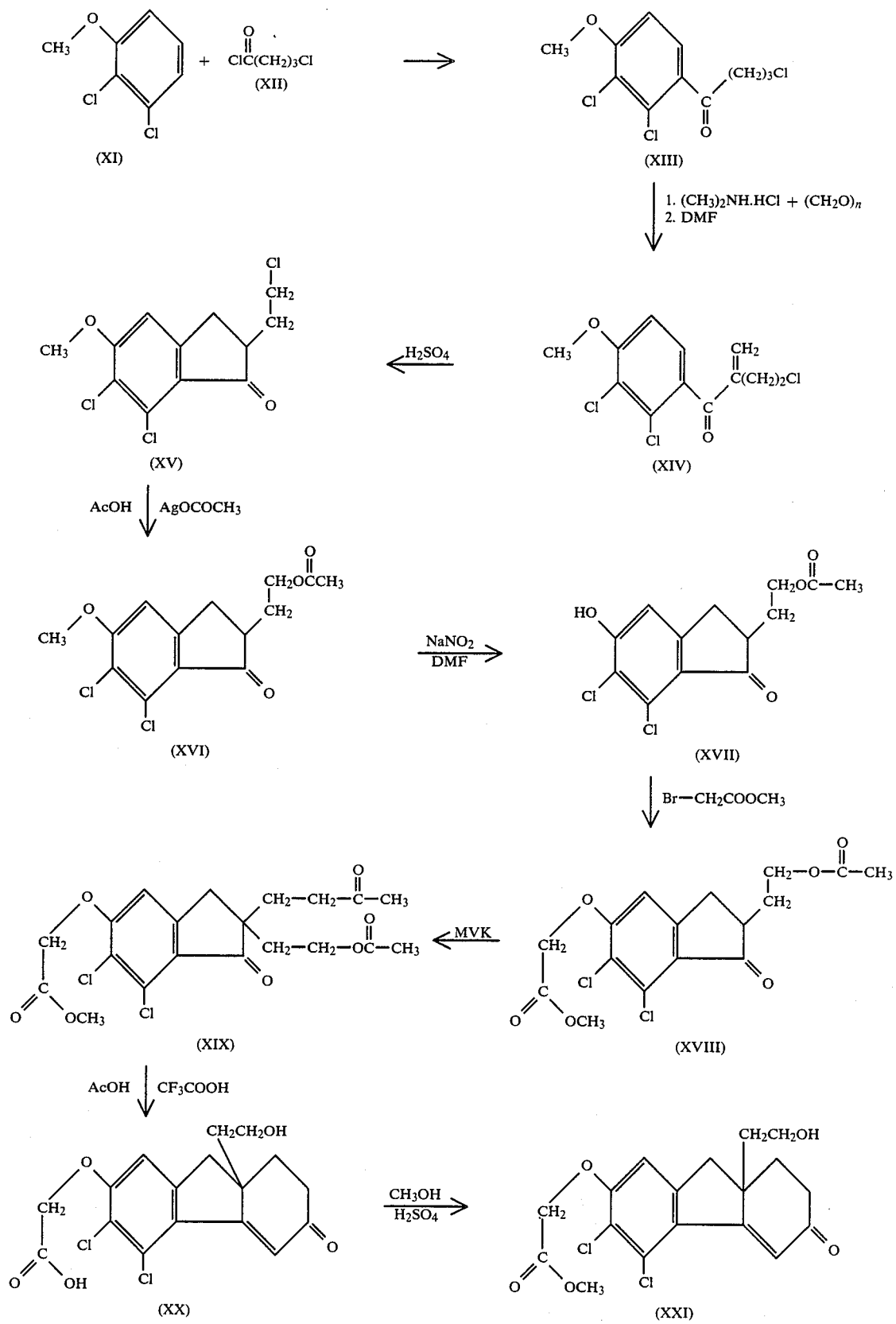

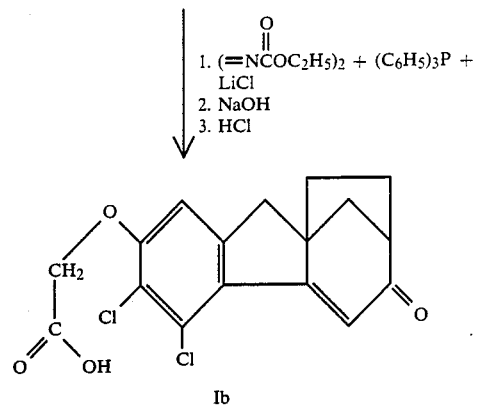

with dimethylamine hydrochloride, paraformaldehyde and a catalytic amount of acetic acid. After stirring the mixture on a steam bath for 1.5 to 3 hours, the intermediate Mannich base is converted to the compound of Formula XIV by the addition of dimethylformamide and stirring on a steam bath for an additional 1.5 to 3 hours.

Cyclization of Compound XIV to indanone XV is effected by treatment with concentrated sulfuric at 25°–40° C. for a period of 8 to 10 hours. Compound XV results upon quenching the reaction mixture in ice.

Replacement of the chloro group of Compound XV by acetoxy to form Compound XVI is accomplished by heating at a temperature of 90°–110° C. for a period of 7 to 12 hours with silver acetate in a mixture of acetic acid containing 0.5–2% of water.

Cleavage of the methoxy group of Compound XVI to form phenol XVII is effected by heating with sodium nitrite in a solvent, such as N,N-dimethylformamide (DMF) for a period of 20 to 30 hours at a temperature of 130°–150° C. Etherification of Compound XVII with methyl bromoacetate to form Compound XVIII is accomplished by heating at 50°–65° C. with N,N-dimethylformamide in the presence of a base, such as potassium carbonate.

Conversion of Compound XVIII to diketone XIX occurs when Compound XVIII is heated with methyl vinyl ketone (MVK) in a solvent, such as tetrahydrofuran or p-dioxane at 45°–60° for a period of 3 to 5 hours in the presence of a catalytic amount of 1,5-diazabicyclo[4.3.0]non-5-ene (DBN) or 1,8-diazabicyclo[5.4.0]undec-7-ene (DBU).

Cyclization and simultaneous saponification of Compound XIX to give Compound XX was accomplished by refluxing Compound XIX with a mixture of acetic acid and trifluoroacetic acid for a period of 2 to 4 days. Esterification of the carboxy group of Compound XX to produce Compound XXI is effected by the synthetic method of refluxing compound XX in methanol containing a little sulfuric acid. The reaction is complete in 12 to 15 hours.

The final steps consist of annulation and saponification of Compound XXI to produce Compound Ib. This is accomplished first by treating a solution of triphenyl phosphine in tetrahydrofuran with a solution of diethyl azodicarboxylate in the same solvents at 0°–5° C. This is followed by the addition of lithium chloride and after 10–20 minutes, the addition of Compound XXI. After stirring for 2 to 4 hours, the intermediate ester is isolated an purified by chromatography and then saponified using an aqueous methanolic solution of sodium hydroxide at reflux for 45 to 75 minutes. Cooling the solution and acidification with hydrochloric acid gives the desired Compound Ib of this invention.

It is to be recognized that Compounds Ia and Ib of this invention possess two asymmetric carbon atoms, therefore, two diastereomers, each consisting of a racemate composed of two enantiomers, are possible. However, the steric constraints of the final annulation lead to the formation of primarily only one racemate which is readily resolved by classical methods accomplished by forming a salt of the racemic mixture with an optically active base such as (+) or (−) amphetamine, (−)cinchonidine, dehydroabietylamine, (+) or (−)-α-methylbenzylamine, (+) or (−)-α-(1-naphthyl)ethylamine, (+)cinchonine, brucine, or strychnine and the like in a suitable solvent such as methanol, ethanol, 2-propanol, benzene, acetonitrile, nitromethane, acetone, and the like. There is formed in the solution two diastereomeric salts one of which is usually less soluble in the solvent than the other. Repetitive recrystallization of the crystalline salt generally affords a pure diastereomeric salt from which is obtained the desired pure enantiomer. The optically pure enantiomer of the compound of Formula Ia or Ib is obtained by acidification of the salt with a mineral acid, isolation by filtration, and recrystallization of the optically pure antipode.

The other optically pure antipode may generally be obtained by using a different base to form the diastereomeric salt. It is of advantage to isolate the partially resolved acid from the filtrates of the purification of the first diastereomeric salt and to further purify this substance through the use of another optically active base. It is especially advantageous to use an optically active base for the isolation of the second enantiomer which is the antipode of the base used for the isolation of the first enantiomer. For example, if (+)-α-methylbenzylamine was used first, then (−)-α-methylbenzylamine is used for the isolation of the second (remaining) enantiomer.

The compounds of Formula Ic which are esters wherein R¹ is lower alkyl or $C(CH_3)_2COOH$ can be prepared

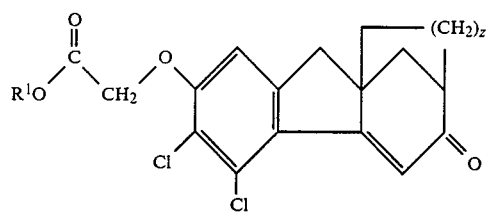

acted with the appropriate alcohol R¹OH, to produce to desired ester (Ic). The initial reaction is conducted at a temperature of 0°–25° C. in a solvent, such as tetrahydrofuran or N,N-dimethylformamide for a period of 15 to 30 minutes. The final step with the alcohol, R¹OH, is carried out in the same reaction medium without isolating XXIII at a temperature of 25°–65° C. for a period of 10 to 24 hours.

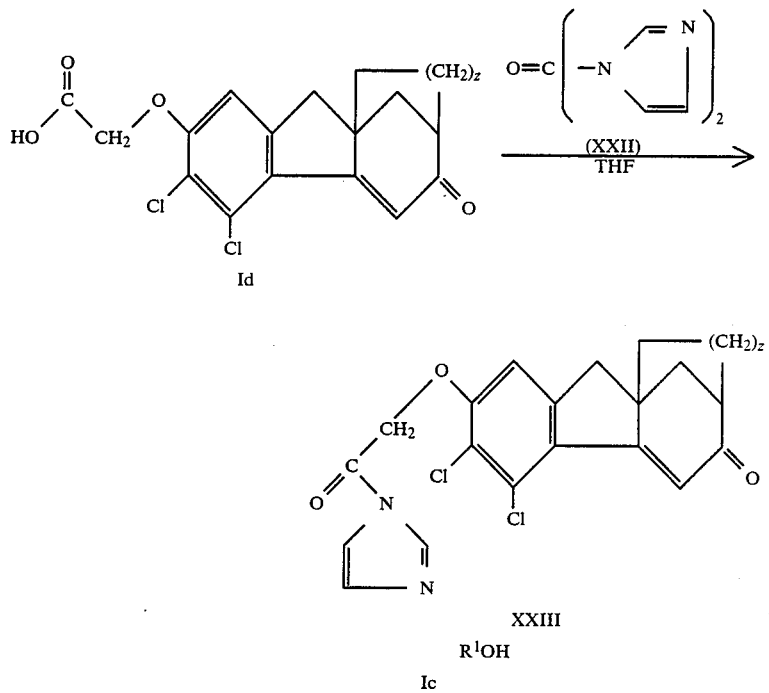

by a variety of methods. A convenient method consists of the following two-step reaction. Treatment of a carboxylic acid of Formula Id where z=1 or 2 (i.e., either Ia or Ib) with 1,1'-carbonyldiimidazole (XXII) to form the imidazole derivative (XXIII) which, in turn, is re- Especially, preferred are the compounds from the alcohol where R¹OH represents 2-hydroxy-2-methylpropionic acid.

The preparation of the compounds of Formula I wherein R=C(=NH)NR²R³ is accomplished by the synthetic method illustrated by the three-step reaction for the synthesis of Ie, wherein z=1 or 2.

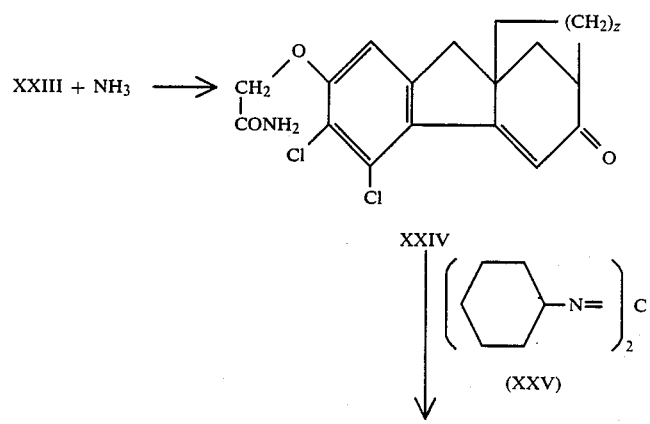

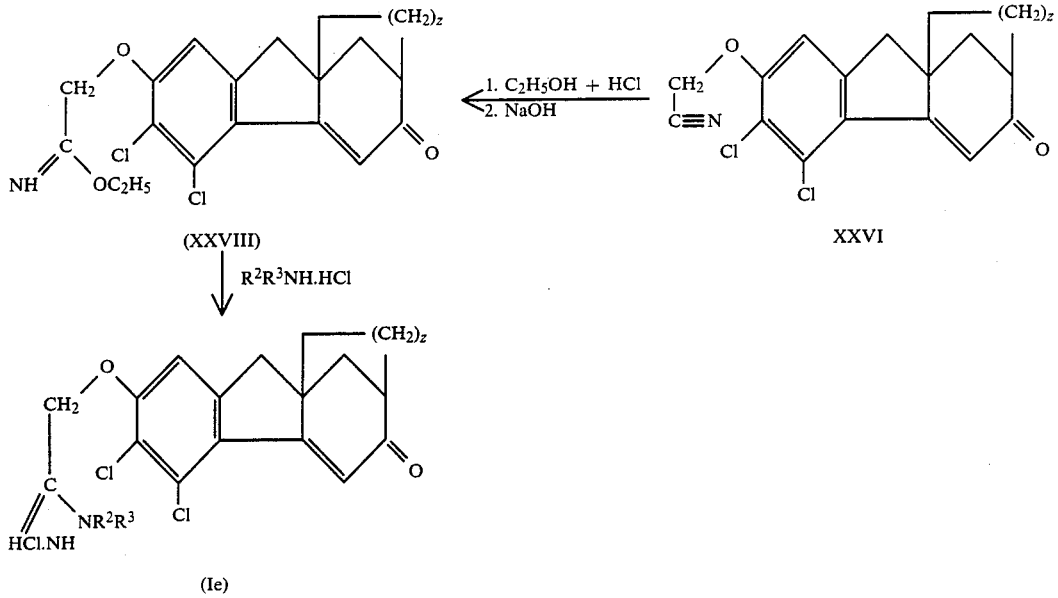

Compound XXIII is treated with ammonia in tetrahydrofuran at ambient temperature for a period of 18 to 30 hours followed by heating at 35°–55° C. for 8 to 24 hours to give the amide of Formula XXIV. Treatment of the amide of Formula XXIV with N,N'-dicyclohexylcarbodiimide (XXV) in pyridine at 10°–25° C. for 20 to 45 minutes followed by stirring at ambient temperature for 2 to 4 hours gives the corresponding nitrile of Formula XXVI. Reaction of the nitrile of Formula XXVI with ethanol and hydrogen chloride in chloroform at −5° to 5° C. for 12 to 20 hours gives the intermediate imido ester of Formula XXVIII upon basification with sodium hydroxide. The reaction of the intermediate XXVIII with ammonium chloride or an amine hydrochloride of Formula $R^2R^3NH.HCl$ in a solution of ethanol and water at ambient temperature for 3 to 5 hours gives the ethanimidamide of Formula Ie.

The pure enantiomers of the alkanimidamides of Formula I can be prepared by classic methods of resolution involving fractional crystallization of salts derived from chiral acids such as (+) and (−)-malic acid, (+) and (−)-dibenzoyltartaric acid, (+) and (−)-α-methoxy-α-(trifluoromethyl)phenylacetic acid, (+) and (−)-tartaric acid, d- and 1-10-camphorsulfonic acid, and 1-α-bromo-camphor-sulfonic acid and the like in a suitable solvent such as methanol, ethanol, 2-propanol, benzene, acetonitrile, nitromethane, acetone and the like. There is formed in the solution, two diastereomeric salts, one of which is usually less soluble in the solvent than the other. Repetitive recrystallization of the crystalline salt generally affords a pure diastereomeric salt from which is obtained the desired pure enantiomer. The optically pure enantiomer of the compound is obtained by reaction of the salt with a base, isolation by filtration and recrystallization of the optically pure antipode.

The other optically pure antipode may generally be obtained by using a different acid to form the diastereomeric salt. It is of advantage to isolate the partially resolved base from the filtrates of the purification of the first diastereomeric salt and to further purify this substance through the use of another optically active acid. It is especially advantageous to use an optically active acid for the isolation of the second enantiomer which is the antipode of the acid used for the isolation of the first enantiomer. For example, if (−)-malic acid was used first, then (+)-malic acid is used for the isolation of the second (remaining) enantiomer.

The preferred method for preparing the pure enantiomers of the alkanimidamides of Formula I is by using the pure enantiomeric forms of the compounds of Formula XXIII in the synthesis of compounds of Formula Ie.

The acid addition salts are prepared by reacting the bases corresponding to the salts of Formula Ie with an appropriate acid, for example, aqueous mineral acids, carboxylic acids or other organic acids, such as hydrochloric acid, sulfuric acid, isethionic acid, methanesulfonic acid, acetic acid and the like. If the compound is already in the form of a salt and a different salt is desired the initial salt may be reacted with a base such as sodium hydroxide to generate the free base which in turn may be reacted with another acid to form a new salt.

The reaction may be conducted in water but it is preferred to conduct the reaction in an organic solvent, such as ether, ethanol, N,N-dimethylformamide and the like.

The preferred salts are the pharmaceutically acceptable salts, such as the hydrochloride salts and the like.

Inasmuch as there are a variety of symptoms and severity associated with grey matter edema, particularly when it is caused by head trauma, stroke, cerebral hemorrhage or embolism, post-operative brain surgery trauma, spinal cord injury, cerebral infections, various brain concussions and elevated intracranial pressure, the precise treatment is left to the practioner. Generally, candidates for treatment will be indicated by the results of the patient's initial general neurological status, findings on specific clinical brain stem functions and findings on computerized axial tomography (CAT), nuclear magnetic resonance (NMR) or position emission tomography (PET) scans of the brain. The sum of the neurological evaluation is presented in the Glascow Coma Score or similar scoring system. Such a scoring system is often valuable in selecting the patients who are candidates for therapy of this kind.

The compounds of this invention can be administered by a variety of established methods, including intravenously, intramuscularly, subcutaneously, or orally. The parenteral route, particularly the intravenous route of administration, is preferred, especially for the very ill and comatose patient. Another advantage of the intravenous route of administration is the speed with which therapeutic brain levels of the drug are achieved. It is of paramount importance in brain injury of the type described to initiate therapy as rapidly as possible and to maintain it through the critical time periods. For this purpose, the intravenous administration of drugs of the type of Formula I in the form of their salts is superior.

A recommended dosage range for treatment is expected to be from 0.05 mg/kg to 20 mg/kg of body weight as a single dose, preferably from 0.5 mg/kg to 10 mg/kg. An alternative to the single dose schedule is to administer a primary loading dose followed by a sustaining dose of half to equal the primary dose, every 4 to 24 hours. When this multiple dose schedule is used the dosage range may be higher than that of the single dose method. Another alternative is to administer an ascending dose sequence of an initial dose followed by a sustaining dose of 1½ to 2 times the initial dose every 4 to 24 hours. For example, 3 intravenous doses of 2, 4 and 6 mg/kg of body weight can be given at 6 hour intervals. If necessary, 4 additional doses of 16 mg/kg of body weight can be given at 12 hour intervals. Another effective dose regimen consists of a continuous intravenous infusion of from 0.05 mg/kg/hr to 3.0 mg/kg/hr. Of course, other dosing schedules and amounts are possible.

One aspect of this invention is the treatment of persons with grey matter edema by concomitant administration of a compound of Formula I or its salts, and an antiinflammatory steroid. These steroids are of some, albeit limited, use in control of white matter edema associated with ischemic stroke and head injury. Steroid therapy is given according to established practice as a supplement to the compound of Formula I as taught elsewhere herein. Similarly, a barbiturate may be administered as a supplement to treatment with a compound of Formula I.

The compounds of Formula I are utilized by formulating them in a pharmaceutical composition such as tablet, capsule or elixir for oral administration. Sterile solutions or suspensions can be used for parenteral administration. A compound or mixture of compounds of Formula I, or its physiologically acceptable salt, is compounded with a physiologically acceptable vehicle, carrier, excipient, binder, preservative, stabilizer, flavor, etc. in a dosage form as called for by accepted pharmaceutical practice.

Illustrative of the adjuvants which may be incorporated in tablets, capsules and the like are the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, lactose, or saccharin; a flavoring agent such as peppermint, oil of wintergreen or cherry. When the dosage unit form is a capsule, it may contain in addition to materials of the above type a liquid carrier such as a fatty oil. Various other materials may be present as coatings or to otherwise enhance the pharmaceutical elegance of the preparation. For instance, tablets may be coated with shellac, sugar or the like. A syrup or elixir may contain the active compound, sucrose as a sweetening agent, methyl and propyl parabens as preservatives, a dye and a flavoring such as cherry or orange flavor.

Sterile compositions for injection or infusion can be formulated according to conventional pharmaceutical practice by dissolving the active substance in a conventional vehicle such as water, saline or dextrose solution by forming a soluble salt in water using an appropriate acid, such as a pharmaceutically acceptable carboxylic acids or mineral acids. Alternatively, a suspension of the active substance in a naturally occurring vegetable oil like sesame oil, coconut oil, peanut oil, cottonseed oil, etc., or a synthetic fatty vehicle like ethyl oleate or the like may be formulated for injection or infusion. Buffer, preservatives, antioxidants and the like can be incorporated as required.

The basic premise for the development of agents for the treatment of brain injury of the types described is based on the studies in experimental head injury by R. S. Bourke et. al. (R. S. Bourke, M. A. Daze and H. K. Kimelberg, Monograph of the International Glial Cell symposium, Leige, Bel. Aug. 29–31, 1977 and references cited therein) and experimental stroke by J. H. Garcia et. al. (J. H. Garcia, H. Kalimo, Y. Kamijyo and B. F. Trump, Virchows Archiv. [Zellopath.], 25, 191 (1977).

These and other studies have shown that the primary site of traumatic brain injury is in the grey matter where the process follows a pattern of insult, edema, ischemia, hypoxia, neuronal death and necrosis followed, in many instances, by irreversible coma or death. The discovery of a drug that specifically prevents the edema would obviate the sequalae.

Experimental head injury has been shown to produce a pathophysiological response primarily involving swelling of astroglial as a secondary, inhibitable process. At the molecular level, the sequence appears to be: trauma, elevation of extracellular $K^+$ and/or release of neurotransmitters, edema, hypoxia and necrosis. Astroglial swelling results directly from a $K^+$-dependent, cation-coupled, chloride transport from the extracellular into the intracellular compartment with a concomitant movement of an osmotic equivalent of water. Thus, an agent that specifically blocks chloride transport in the astroglia is expected to block the edema caused by trauma and other insults to the brain. It is also important that such chloride transport inhibitors be free or relatively free of side effects, particularly those characteristics of many chloride transport inhibitors, such as diuretic properties. Compounds of the type illustrated by Formula I exhibit the desired effects on brain edema and are relatively free of renal effects.

That this approach is valid has been demonstrated by the correlation of the in vitro astroglial edema inhibiting effects of chloride transport inhibitors with their ability to reduce the mortality of animals receiving experimental in vivo head injury. As a final proof, one compound (ethacrynic acid) which exhibited activity both in vitro and in vivo assays was effective in reducing mortality in clinical cases of head injury. These studies are described in the Journal of Medicinal Chemistry, Volume 25, page 567 (1982), which is hereby incorporated by reference.

Three major biological assays can be used to demonstrate biological activity of the compounds. The (1) in vitro cat cerebrocortical tissue slice assay, (2) the in vitro primary rat astrocyte culture assay and (3) the in vivo cat head injury assay. The first assay, the in vitro cat cerebrocortical tissue slice assay has been described by Marshall, L. F.; Shapiro, H. M.; Smith, R. W. In "Seminars in Neurological Surgery: Neural Trauma"; Popp, A. J.; Bourke, R. S.; Nelson, L. R.; Kimelberg, H, K,. Eds.; Raven Press: New York, 1979; p. 347, by Bourke, R. S.; Kimelberg, H, K.; Daze, M. A. in Brain Res. 1978, 154, 196, and by Bourke, R. S.; Kimelberg, H. K,; Nelson, L. R. in Brain Res. 1976, 105, 309. This method constitutes a rapid and accurate method of determining the intrinsic chloride inhibitory properties of the compounds of the invention in the target tissue.

The second assay method involves the in vitro primary rat astrocyte assay. The method has been described by Kimelberg, H. K.; Biddlecome, S.; Bourke, R. S. in Brain Res. 1979, 173, 111, by Kimelberg, H. K.; Bowman, C.; Biddlecome, S.; Bourke, R. S., in Brain Res. 1979, 177, 533, and by Kimelberg, H. K.; Hirata, H. in Soc. Neurosci. Abstr. 1981, 7, 698. This method is used to confirm the chloride transport inhibiting properties of the compounds in the pure target cells, the astrocytes.

The third assay method, the in vivo cat head injury assay has been described by Nelson, L. R.; Bourke, R. S.; Popp, A. J.; Cragoe, E. J. Jr.; Signorelli, A.; Foster, V. V.; Creel, in Marshall, L. F.; Shapiro, H. M.; Smith, R. W. In "Seminars in Neurological Surgery: Neural Trauma"; Popp, A. J.; Bourke, R. S.; Nelson, L. R.; Kimelberg, H. K., Eds.; Raven Press: New York, 1979; p. 297.

This assay consists of a highly relevant brain injury in cats which is achieved by the delivery of rapid repetitive acceleration-deceleration impulses to the animal's head followed by exposure of the animals to a period of hypoxia. The experimental conditions of the assay can be adjusted so that the mortality of the contrl animals falls in the range of about 25 to 75%. Then, the effect of the administration of compounds of this invention in reducing the mortality over that of the control animals in concurrent experiments can be demonstrated.

Using the in vitro cat cerebrocortical tissue slice assay, described in Example 1, compounds of the present invention can be tested for activity. This test provides the principal in vitro evaluation and consists of a determination of concentration vs. response curve. The addition of $HCO_3^-$ to isotonic, $K^+$-rich saline-glucose incubation media is known to specifically stimulate the transport of $Cl^-$ coupled with $Na^+$ and an osmotic equivalent of water in incubating slices of mammalian cerebral cortex. Experiments have demonstrated that the tissue locus of swelling is an expanded astroglial compartment. Thus, the addition of $HCO_3^-$ to incubation media stimulates statistically significant and comparable increases in cerebrocortical tissue swelling and ion levels. After addition of drug to the incubation media, detailed drug concentration-response curves are then obtained. The data are expressed as percent $HCO_3^-$-stimulated swelling vs. drug concentration, from which the concentration of drug providing 50% inhibition of $HCO_3^-$-stimulated swelling ($I_{50}$ in molarity) is interpolated.

Using this assay for racemic [(5,6-dichloro-3-oxo-2,9a-propano-2,3,9,9a-tetrahydro-1H-fluoren-7-yl)oxy]acetic acid described in Example 2, Step H) the following value for percentage inhibition of tissue swelling (% inhib) were observed at the given molar concentrations [conc. (M)].

| Conc. M | % Inhib. |
|---|---|
| $10^{-6}$ | 81 |
| $10^{-7}$ | 54 |
| $10^{-8}$ | 29 |
| $10^{-9}$ | 10 |

The following examples are included to illustrate the in vitro cerebrocortical tissue slice assay, the preparation of representative compounds of Formula I and representative dosage forms of these compounds. It is intended that the specification and examples be considered as exemplary only, with the true scope and spirit of the invention being indicated by the following claims. All temperatures in the examples are in Centigrade unless otherwise indicated.

EXAMPLE 1

In Vitro Cerebrocortical Tissue Slice Assay

Adult cats of 2–3 kg body weight are employed in tissue slice studies. Prior to sacrifice, the animals are anesthetized with ketamine hydrochloride (Ketaset), 10 mg/kg intramuscularly. Eight (three control, five experimental) pial surface cerebrocortical tissue slices (0.5-mm thick; approximately 150 mg initial fresh weight) are cut successively with a calibrated Stadie-Riggs fresh tissue microtome without moistening and weighed successively on a torsion balance. During the slice preparation all operations except weighing are confined to a humid chamber. Each slice is rapidly placed in an individual Warburg flask containing 2 ml of incubation medium at room temperature. The basic composition of the incubation media, in millimoles per liter, is as follows: glucose, 10; $CaCl_2$, 1.3; $MgSO_4$, 1.2; $KHSO_4$, 1.2; Hepes (N-2-hydroxyethylpiperazine-N'-2-ethanesulfonic acid, titrated with NaOH to pH 7.4), 20. Except when adding $HCO_3^-$, the osmolarity of the media is maintained isosmotic (approximately 285 mOsm/L) by reciprocal changes of $Na^+$ or $K^+$ to achieve a concentration of $K^+$ of 27 mM. The basic medium was saturated with oxygen by bubbling pure oxygen through the solution for 30 minutes before use. When added, $NaHCO_3$ or triethylammonium bicarbonate (TEAB) is initially present in the sidearm of each flask at an initial concentration of 50 mM in 0.5 ml of complete medium. Nonbicarbonate control slices are incubated at 37° C. in 2.5 ml of basic medium for 60 minutes. Bicarbonate control slices are similarly incubated for an initial 20 minutes at 37° C. in 2.0 ml of basic medium to which is added from the sidearm an additional 0.5 ml of incubation medium containing 50 mM $HCO_3^-$, which, after mixing, results in a $HCO_3^-$ concentration of 10 mM and a total volume of 2.5 ml. The incubation is continued for an additional 40 minutes. The various compounds to be tested are dissolved by forming the hydrochloride salts in water. When only the free bases are available, the hydrochloride salts are formed by treating the free base with a molar equivalent of hydrochloric acid and diluting to the appropriate concentrations. Just prior to incubation, all flasks containing $HCO_3^-$ are gassed for 5 minutes with 2.5% $CO_2/97.5\%$ $O_2$ instead of 100% $O_2$.

Following the 60-minute incubation period, tissue slices are separated from incubation medium by filtration, reweighed, and homogenized in 1N $HClO_4$ (10% w/v) for electrolyte analysis. The tissue content of ion is expressed in micromoles per gram initial preswelling fresh weight. Control slice swelling is expressed as microliters per gram initial preswelling fresh weight. The effectiveness of an inhibitor at a given concentration is measured by the amount of $HCO_3{}^-$-stimulated swelling that occurred in its presence, computed as a percent of the maximum possible. Tissue and media $Na^+$ and $K^+$ levels are determined by emission flame photometry with $Li^+$ internal standard; $Cl^-$ levels are determined by amperometric titration. Tissue viability during incubation is monitored by manometry.

EXAMPLE 2

[(5,6-Dichloro-3-oxo-2,9a-propano-2,3,9,9a-tetrahydro-1H-fluoren-7-yl)oxy]acetic acid

Step A 2,3-Dichloro-4-(5-chloropentanoyl)-anisole 2,3-Dichloroanisole (160 g, 0.9 mole) and 5-chloropentanoyl chloride (140 g, 0.9 mole) were dissolved in methylene chloride (400 ml). The solution was cooled in an ice bath while aluminum chloride (130 g, 0.99 mole) was added portionwise over one hour. The ice bath was removed and the mixture was stirred at ambient temperature for 20 hours followed by refluxing for one hour. The mixture was cooled, poured onto crushed ice and extracted with methylene chloride. The combined organic extracts were washed with 5% sodium hydroxide solution, then with water and dried over $Na_2SO_4$. The solvent was removed in vacuo leaving 229 g of 2,3-dichloro-b 4-(5-chloropentanoyl)anisole, b.p. 165°–170°/0.5 mm.

Anal. Calc'd for $C_{12}H_{13}Cl_3O_2$: C, 48.76; H, 4.43%. Found: C, 48.32; H, 4.30%.

Step B 2-(Dimethylaminomethyl)-5-chloro-1-(2,3-dichloro-4-methoxyphenyl)-1-pentanone 2,3-Dichloro-4-(5-chloropentanoyl)anisole (29.5 g, 0.1 mole) and N,N,N′,N′-tetramethyldiaminomethane (25.5 g, 0.249 mole) were stirred and heated at 50° C. and then acetic anhydride (36.8 g, 0.36 mole) was added dropwise with stirring at such a rate that the temperature rose to 100° C. After heating at 95° C. for an additional 2 hours, the mixture was kept at ambient temperature for 15 hours, poured into crushed ice (400 g), strongly basified with 10 normal sodium hydroxide and extracted with ether. The ether extract was dried over $Na_2SO_4$ and the solvent removed in vacuo to give 2-(dimethylaminomethyl)-5-chloro-1-(2,3-dichloro-4-methoxyphenyl)-1-pentanone as a viscous oil.

Anal. Calc'd for $C_{15}H_{19}C_{12}NO_2$: C, 48.76; H, 4.43%. Found: C, 48.70; H, 4.40%.

Step C 2-(3-Chloropropyl)-6,7-dichloro-2,3-dihydro-5-methoxy-1H-inden-1-one 2-(Dimethylaminomethyl)-5-chloro-1-(2,3-dichloro-4-methoxyphenyl)-1-pentanone (6.1 g, 0.019 mole) was added in portions to well-stirred concentrated sulfuric acid (25 ml). The temperature rose to 39° C. after which the mixture was stirred at ambient temperature for an additional two hours. The mixture was poured into crushed ice and the resulting precipitate removed by filtration, washed with water, dried and then recrystallized from a mixture of tetrahydrofuran and ether to give 2-(3-chloropropyl)-6,7-dichloro-2,3-dihydro-5-methoxy-1H-inden-1-one, 5 g, m.p. 130°–132° C.

Anal. Calc'd for $C_{13}H_{12}Cl_3O_2$: C, 50.75; H, 4.26%. Found: C, 50.85; H, 4.42%.

Step D 2-(3-Chloropropyl)-6,7-dichloro-2,3-dihydro-5-methoxy-2-(3-oxobutyl)-1H-inden-1-one 2-(3-Chloropropyl)-6,7-dichloro-2,3-dihydro-5-methoxy-1H-inden-1-one (59 g, 0.20 mole) was dissolved in tetrahydrofuran (50 ml) and 1,5-diazabicyclo[4.3.0]non-5-ene (DBN) (3 ml) added. The mixture was stirred and methyl vinyl ketone (28.3 g, 0.404 mole) added dropwise over 30 minutes. The temperature rose from 22° C. to 35° C. over the addition period. The mixture was stirred for an additional hour at ambient temperature, then poured into cold water. The solid that separated was removed by filtration, washed with water, dried and recrystallized from a mixture of tetrahydrofuran and ether to give 2-(3-chloropropyl)-6,7-dichloro-2,3-dihydro-5-methoxy-2-(3-oxobutyl)-1H-inden-1-one, 58.5 g, m.p. 120°–122° C.

Anal. Calc'd for $C_{17}H_{19}Cl_3O_3$: C, 54.06; H, 5.07%. Found: C, 54.26; H, 5.25%.

Step E 9a-(3-Chloropropyl)-5,6-dichloro-7-methoxy-1,2,9,9a-tetrahydro-3H-fluoren-3-one 2-(3-Chloropropyl)-6,7-dichloro-2,3-dihydro-5-methoxy-2-(3-oxobutyl)-1H-inden-1-one (36 g, 0.0053 mole) was dissolved in methanol (4.75 ml) containing 10% aqueous sodium hydroxide (190 ml). Then stirred and refluxed for 3 hours. The solution was cooled, poured into crushed ice, acidified with hydrochloric acid and the solid that separated removed by filtration. The solid washed on the filter with water, dried and recrystallized from a mixture of tetrahydrofuran and ether to give 9a-(3-chloropropyl)-5,6-dichloro-7-methoxy-1,2,9,9a-tetrahydro-3H-fluoren-3-one, 15 g, m.p. 183°–185° C.

Anal. Calc'd for $C_{17}H_{17}Cl_3O_2$: C, 56.76; H, 4.77%. Found: C, 57.14; H, 5.00%.

Step F 5,6-Dichloro-7-hydroxy-2,9a-propano-1,2,9,9a-tetrahydro-3H-fluoren-3-one 9a-(3-Chloropropyl)-5,6-dichloro-7-methoxy-1,2,9,9a-tetrahydro-3H-fluoren-3-one (6 g, 0.0167 mole) was added to a mixture of 35% hydrobromic acid in acetic acid (24 ml) and 48% aqueous hydrobromic acid (36 ml) and the mixture refluxed for 5½ hours. The reaction mixture was poured into cold water (350 ml) and extracted with a mixture of 20% tetrahydrofuran in ether. The combined organic extracts were extracted with 2% aqueous sodium hydroxide solution and the aqueous extract acidified with hydrochloric acid. The solid that separated was removed by filtration, washed with water and dried. The solid was chromatographed on a column of silica gel (300 g), eluting with a mixture of acetic acid/acetone/toluene, 5/5/90. The appropriate fractions were combined and evaporated in vacuo to give 2.6 g of 5,6-dichloro-7-hydroxy-2,9a-propano-1,2,9,9a-tetrahydro-3H-fluoren-3-one, m.p. 257°–259° C.

Anal. Calc'd for $C_{16}H_{14}Cl_2O_2$: C, 62.15; H, 4.56; Cl, 22.94%. Found: C, 62.19; H, 4.65; Cl, 23.16%.

Step G

Methyl [(5,6-Dichloro-3-oxo-2,9a-propano-2,3,9,9a-tetrahydro-1H-fluoren-7-yl)oxy]-acetate 5,6-Dichloro-7-hydroxy-2,9a-propano-1,2,9,9a-tetrahydro-3H-fluoren-3-one (5 g, 0.016 mole) was dissolved in N,N-dimethylformamide (25 ml) and treated with potassium carbonate (4.8 g, 0.035 mole). The mixture was stirred for 15 minutes on a steam bath then cooled to 60° C. and methyl bromoacetate (4.9 g, 0.032 mole) added and stirring at 60° C. continued for 5 hours. The mixture was cooled, poured into water (300 ml) and extractd with ether. The ether extract was washed with water, dried over $Na_2SO_4$ and the solvent removed in vacuo. The residue was purified by column chromatography using silica gel (300 g), eluting with an acetic acid/acetone/toluene, 5/5/90 mixture. Combination of the appropriate fractions and evaporation of the solvents in vacuo gave methyl [(5,6-dichloro-3-oxo-2,9a-propano-2,3,9,9a-tetrahydro-1H-fluoren-7-yl)oxy]acetate, 3.5 g which upon recrystallization from a mixture of tetrahydrofuran and ether melted at 142°–146° C.

Anal. Calc'd for $C_{19}H_{18}Cl_2O_4$: C, 58.85; H, 4.76%. Found: C, 59.64; H, 4.48%.

Step H

[(5,6-Dichloro-3-oxo-2,9a-propano-2,3,9,9a-tetrahydro-1H-fluoren-7-yl)oxy]acetic acid Methyl [(5,6-dichloro-3-oxo-2,9a-propano-2,3,9,9a-tetrahydro-1H-fluoren-7-yl)oxy]acetate (1.5 g, 0.00315 mole) was treated with a mixture of methanol (25 ml) and 2% aqueous sodium hydroxide solution (100 ml). The mixture was stirred and heated on a stream bath for one hour. The clear solution was cooled, acidified with hydrochloric acid and the solid that formed was removed by filtration, washed with water and dried to give 1.4 g of [(5,6-dichloro-3-oxo-2,9a-propano-2,3,9,9a-tetrahydro-1H-fluoren-7-yl)oxy]acetic acid. After recrystallization from acetonitrile followed by column chromatography with silica gel (150 g), eluting with a mixture of acetic acid/tetrahydrofuran/methylene chloride, 5/5/90, pooling the appropriate fractions, evaporating the solvent in vacuo and recrystallization of the residue from acetonitrile, the compound melts at 243°–245° C.

Anal. Calc'd for $C_{18}H_{16}Cl_2O_4$: C, 58.87; H, 4.76%. Found: C, 58.54; H, 4.56%.

EXAMPLE 3

Resolution of Racemic [(5,6-dichloro-3-oxo-2,9a-propano-2,3,9,9a-tetrahydro-1H-fluoren-7-yl)oxy]acetic acid (3.67 g, 10 mMole) in acetonitrile (270 ml) is heated to boiling and cinchonine (2.95 g, 10 mmol) was added. The solution was stirred at 5° C. for 24 hours and the solid that separated was filtered off, washed with aceto and the filtrate was (I) saved. The salt was recrystallized from acetonitrile and the product removed by filtration, dried, treated with 1 normal hydrochloric acid (50 mL) and extracted with 20% tetrahydrofuran in ether to give the pure enantiomer. The extract was dried over $MgSO_4$; the solvent was evaporated in vacuo and the residue recrystallized to give the pure enantiomer of [(5,6-dichloro-3-oxo-2,9a-propano-2,3,9,9a-tetrahydro-1H-fluoren-7-yl)oxy]acetic acid.

Filtrate (I) was evaporated in vacuo, treated with 2 normal hydrochloric acid (45 mL), extracted with 20% tetrahydrofuran in ether and the extract was dried over $MgSO_4$. The solvent was evaporated in vacuo and the residue dissolved in acetonitrile (250 L), heated to boiling and cinchonidine (2.95 g, 10 mmol) was added. The solution was cooled to 5° C. and stirred for 24 hours. The solid that separated was recrystallized and worked up as described above for the other (opposite) enantiomer.

EXAMPLE 4

[(5,6-Dichloro-2,9a-ethano-3-oxo-2,3,9,9a-tetrahydro-1H-fluoren-7-yl)oxy]acetic acid

Step A 2,3-Dichloro-4-(4-(4-chlorobutyryl)anisole 2,3-Dichloroanisole (120 g, 0.68 mole) and 4-chlorobutyryl chloride (100 g, 0.709 mole) was dissolved in methylene chloride (425 ml) and aluminum chloride (98.8 g, 0.741 mole) added portionwise with stirring under anhydrous conditions over a period of 30 minutes. The temperature gradually rose to 32° C. Stirring was continued at ambient temperature for 3 hours longer and then the mixture was poured into crushed ice (1 kg) containing concentrated hydrochloric acid (80 ml). The layers were separated and the aqueous layer extracted with methylene chloride and then with ether. The combined organic layers were washed with dilute hydrochloric acid, brine, dilute sodium hydroxide solution and finally with brine.

The solvents were removed in vacuo and the residue dissolved in ether, then washed with dilute sodium hydroxide solution and finally with water. The organic layer was dried over $MgSO_4$ and the solvent removed by evaporation in vacuo. The residue was triturated with hexane, filtered, washed with hexane and dried. The yield of 2,3-dichloro-4-(4-chlorobutyryl)anisole was 144.5 g, m.p. 55°–57° C.

Step B 2,3-Dichloro-4-(2-methylene-4-chlorobutyryl)anisole 2,3-Dichloro-4-(4-chlorobutyryl)anisole (28.1 g, 0.1 mole), dimethylamine hydrochloride (36.7 g, 0.45 mole) and paraformaldehyde (7.65 g, 0.255 mole) were united and glacial acetic acid (2.6 ml) added. The mixture was stirred and heated on a steam bath under anhydrous conditions for 2 hours. Then the mixture was treated with N,N-dimethylformamide and heating and stirring on a steam bath continued for another 2 hours. The mixture was poured into a mixture of crushed ice and water (800 ml) and extracted with ether.

The combined organic extracts were washed with water, dried over $MgSO_4$ and the solvent removed by evaporation in vacuo. The residue consisted of 2,3-dichloro-4-(2-methylene-4-chlorobutyryl)anisole, 14.2 g, m.p. 58°–60° C.

Step C 2-(2-Chloroethyl)-6,7-dichloro-5-methoxy-1H-inden-1-one 2,3-Dichloro-4-(2-methylene-4-chlorobutyryl)anisole (43 g, 0.146 mole) was dissolved in methylene chloride (20 ml) and the solution added to concentrated sulfuric acid (165 ml) gradually with stirring over a period of 30 minutes. The temperature gradually rose to 39° C. The mixture was stirred at ambient temperature for another 16 hours, then poured into a mixture of crushed ice and water (800 ml).

The mixture was extracted with methylene chloride and then with ether. The combined organic extracts were dried over MgSO₄ and the solvents removed by evaporation in vacuo. The residue weighed 38 g. Upon trituration of this solid with 2-propanol, filtering, washing with 2-propanol and drying, there was obtained 2-(2-chloroethyl)-6,7-dichloro-5-methoxy-1H-inden-1-one, m.p. 103°–105° C.

Step D 2-(Acetoxyethyl)-6,7-dichloro-5-methoxy-1H-inden-1-one 2-(2-Chloroethyl)-6,7-dichloro-5-methoxy-1H-inden-1-one (18.4 g, 0.0619 mole) and silver acetate (22.7 g, 0.1362 mole) were suspended in acetic acid (225 ml) and water (2 ml) and the mixture stirred and heated at 105° C. for 9 hours and at ambient temperature for 16 hours. The mixture was filtered and the residue on the funnel washed with ethyl acetate. The combined filtrate were evaporated in vacuo and the residue suspended in water. The mixture was extracted first with 10% tetrahydofuran in ether, then with methylene chloride and finally with ethyl acetate. The combined organic extracts were washed with water, then with brine. After drying over MgSO₄ the combined organic extracts were evaporated in vacuo. The residue was treated with warm ethyl acetate (10 ml) and tetrahydrofuran (10 ml) and then cooled. The solid that formed was removed by filtration with an equal mixture of ethyl acetate and hexane and dried to give 2-(acetoxyethyl)-6,7-dichloro-5-methoxy-1H-inden-1-one, 8.1 g, m.p. 134°–136° C.

Anal. Calc'd for $C_{14}H_{14}Cl_2O_4$: C, 53.01; H, 4.45%. Found: C, 53.16; H, 4.41%.

Step E 2-(2-Acetoxyethyl)-6,7-dichloro-2,3-dihydro-5-hydroxy-1H-inden-1-one 2-(Acetoxyethyl)-6,7-dichloro-5-methoxy-1H-inden-1-one (6.34 g, 0.02 mole) and sodium nitrite (8.28 g, 0.12 mole) in dry N,N-dimethylformamide (150 ml) were heated and stirred at 140° C. in an atmosphere of dry nitrogen for 20 hours. The mixture was cooled and 115 ml of the N,N-dimethylformamide removed by distillation in vacuo. The residue was poured into a mixture of crushed ice and water containing acetic acid (12 ml). The mixture was extracted with a mixture of 20% tetrahydrofuran in ether, then methylene chloride and finally ethyl acetate. The combined organic extracts were washed with water and finally dried over MgSO₄. The solvents were removed by evaporation in vacuo to give a residue consisting of 2-(2-acetoxyethyl)-6,7-dichloro-2,3-dihydro-5-hydroxy-1H-inden-1-one weighing 6.1 g.

Step F

Methyl{[2-(2-Acetoxyethyl)-6,7-dichloro-2,3-dihydro-1-oxo-1H-inden-5-yl]oxy}acetate 2-(2-Acetoxyethyl)-6,7-dichloro-2,3-dihydro-5-hydroxy-1H-inden-1-one (5.8 g, 0.0191 mole) was dissolved in dry N,N-dimethylformamide (35 ml) and potassium carbonate (3.97 g, 0.0287 mole) added. The mixture was stirred while methyl bromoacetate (3.52 g, 0.023 mole) was added while maintaining a temperature of 55°–60° C. Stirring at 60°–65° C. was continued for 3 hours and then the mixture was cooled and poured into a mixture of crushed ice and water (250 ml) containing concentrated hydrochloric acid (10 ml). The mixture was extracted first with 20% tetrahydrofuran in ether and then with methylene chloride. The combined organic extracts were washed first with water and then with brine and finally dried over MgSO₄. The solvent was evaporated in vacuo to give 6.9 g of product. Purification was effected by column chromatography using silica gel (300 g) and eluting with methylene chloride/tetrahydrofuran, 50/1 to give 3.3 g of methyl {[2-(2-acetoxyethyl)-6,7-dichloro-2,3-dihydro-1-oxo-1H-inden-5-yl]oxy}acetate m.p. 111°–113° C.

Step G

Methyl{[2-(2-Acetoxyethyl)-6,7-dichloro-2,3-dihydro-1-oxo-2-(3-oxobutyl)-1-H-inden-5-yl]oxy}acetate Methyl}[2-(2-acetoxyethyl)-6,7-dichloro-2,3-dihydro-1-oxo-1H-inden-5-yl]oxy}acetate (3.2 g, 0.00853 mole) in dry tetrahydrofuran (30 ml) was stirred and warmed to 40° C. and 1,5-diazobicyclo[4.3.0]non-5-ene (DBN) (50 µl) added. Finally, methyl vinyl ketone (1.2 g, 0.017 mole) was added and the mixture stirred and heated at 50°–52° C. for 100 minutes. More DBN (2 drops) and methyl vinyl ketone (0.4 ml) were added and stirring and heating at 40° C. continued for 4 hours longer. The mixture was cooled, diluted with ethyl actate (50 ml) and poured into ice water (250 ml) containing acetic acid (1 ml). The layers were separated and the aqueous layer extracted first with methylene chloride and then with ether. The combined organic layer and extracts were washed with water and dried over MgSO₄. The solvents were removed by evaporation in vacuo to give 3.8 g of methyl{[2-(2-acetoxyethyl)-6,7-dichloro-2,3-dihydro-1-oxo-2-(3-oxobutyl)-1H-inden-5-yl]oxy}acetate.

Step H

{[9a-(2-Hydroxyethyl)-5,6-dichloro-3-oxy-2,3,9,9a-tetrahydro-1H-fluoren-7-yl]oxy}acetic acid Methyl{[2-(2-acetoxyethyl)-6,7-dichloro-2,3-dihydro-1-oxo-2-(2-oxobutyl)-1H-inden-5-yl]oxy}acetate (3.8 g, 0.0088 mole) was dissolved in a mixture of acetic acid (60 ml) and trifluoroacetic acid (40 ml), stirred and refluxed for 3 days. The solvents were evaporated in vacuo and the residue treated with water and extracted first with a 20% solution of tetrahydrofuran in ether and then with methylene chloride. The combined organic extracts were filtered, washed with water and dried over MgSO₄. The solvvents were removed by evaoration in vacuo and the residue dissolved in a mixture of methanol (40 ml), 1 normal sodium hydroxide (20 ml) and water (20 ml). The mixture was stirred and refluxed for 75 minutes. The mixture was diluted with water (150 ml), acidified with concentrated hydrochloric acid and extracted first with ether and then with methylene chloride.

The organic extracts were washed with water, dried over MgSO₄ and the solvents removed by evaporation in vacuo. The residue was recrystallized first from acetonitrile and then from a mixture of acetic acid (37 ml) and water (9 ml) to give {[9a-(2-hydroxyethyl)-5,6-dichloro-3-oxy-2,3,9,9a-tetrahydro-1H-fluoren-7-yl]oxy}-acetic acid, m.p. 230° C.

Anal Calc'd for $C_{17}H_{16}Cl_2O_5$: C, 55.00; H, 4.31%. Found: C, 55.05; H, 4.47%.

Step I

Methyl {[5,6-Dichloro-9a-(2-hydroxyethyl)-3-oxo-2,3,9,9a-tetrahydro-1H-fluoren-7-yl]oxy}acetate {[9a-(2-Hydroxyethyl)-5,6-dichloro-3-oxo-2,3,9,9a-tetrahydro-1H-fluoren-7-yl]oxy}acetic acid (2 g, 0.00538 mole) was dissolved in methanol (170 ml) containing concentrated sulfuric acid (1 ml) and refluxed for 16 hours. The mixture was evaporated to 50 ml and diluted with water (300 ml). The mixture was extracted with methylene chloride and the combined extracts diluted with ether. The extracts were washed with water, then with brine and dried over MgSO₄. The solvents were evaporated in vacuo to give 1.49 g of residue which was purified by column chromatography using 140 g of silica gel, eluting with methanol/methylene chloride 3.5/96.5 to give 330 mg of methyl {[5,6-dichloro-9a-(2-hydroxyethyl)-3-oxo-2,3,9,9a-tetrahydro-1H-fluoren-7-yl]oxy}acetate.

Step J

[(5,6-Dichloro-2,9a-ethano-3-oxo-2,3,9,9a-tetrahydro-1H-fluoren-7-yl)oxy]acetic acid To a solution of triphenylphosphine (2.55 g, 0.0097 mole) in tetrahydrofuran (15 ml) in a dry nitrogen atmosphere was added diethyl azodicarboxylate (1.66 g, 0.095 mole) in tetrahydrofuran (10 ml) at 0°–5° C. After 15 minutes lithium chloride (0.825 g, 0.0195 mole) was added followed by a solution of methyl {[(5,6-dichloro-9a-(2-hydroxyethyl)-3-oxo-2,3,9,9a-tetrahydro-1H-fluoren-7-yl]oxy}acetate (1.0 g, 0.0026 mole). After stirring for 3 hours, the reaction mixture was poured into ice water (300 ml), extracted with ether, washed with brine and dried over MgSO₄. The solvents were removed by evaporation in vacuo and the residue chromatographed on silica gel (145 g), eluting with tetrahydrofuran/methylene chloride 1.5/98.5. Evaporation of the pertinent fractions gave 500 mg of the methyl ester of the product which was dissolved in a mixture of methanol (15 ml), water (42 ml) and 1 normal sodium hydroxide (3 ml) and refluxed for one hour. The reaction mixture was poured into ice water containing dilute hydrochloric acid and extracted with ether. The combined organic extracts were washed with water, dried over MgSO₄ and the solvent evaporated in vacuo. The residue consisted of [(5,6-dichloro-2,9a-ethano-3-oxo-2,3,9,9a-tetrahydro-1H-fluoren-7-yl)oxy]acetic acid, 440 mg, m.p. 254°–256° C.

Anal Calc'd for $C_{17}H_{14}Cl_2O_4$: C, 57.81; H, 4.00; Cl, 20.08%. Found: C, 57.71; H, 3.95; Cl, 20.30%.

EXAMPLE 5

Resolution of [(5,6-Dichloro-2,9a-ethano-3-oxo-2,3,9,9a-tetrahydro-1H-fluoren-7-yl)oxy]acetic acid Carrying out the reaction as described in Example 3 except that the [(5,6-dichloro-2-oxo-2,9a-propano-2,3,9,9a-tetrahydro-1H-fluoren-7-yl)oxy]acetic acid is replaced by an equimolar amount of [(5,6-dichloro-2,9a-ethano-3-oxo-2,3,9,9a-tetrahydro-1H-fluoren-7-yl)oxy]acetic acid, there is obtained the two enantiomers of [(5,6-dichloro-2,9a-ethano-3-oxo-2,3,9,9a-tetrahydro-1H-fluoren-7yl)oxy]acetic acid.

EXAMPLE 6

1-Carboxy-1-methylethyl [(5,6-dichloro-2,9a-ethano-3-oxo-2,3,9,9a-tetrahydro-1H-fluoren-7-yl)oxy]acetate

[(5,6-Dichloro-2,9a-ethano-3-oxo-2,3,9,9a-tetrahydro-1H-fluoren-7-yl)-oxy]acetic acid (3.53 mole, 0.01 mole) is dissolved in dry tetrahydrofuran (20 ml). 1,1'-carbonyldiimidazole (3.2 g, 0.01 mole) is added and the mixture stirred at 20° C. for one hour. 2-Hydroxy-2-methylpropionic acid (1.05 g, 0.01 mole) is added and the mixture stirred for 18 hours at 20° C. The solvent is removed by evaporation in vacuo and the residue purified by column chromatography on silica gel, eluting with a mixture of methylene chloride, tetrahydrofuran and acetic acid, 100/2/1 (V.V.V.). Combining the appropriate fractions and evaporating the solvent in vacuo gave 1-carboxy-1-methylethyl [(5,6-dichloro-2,9a-ethano-3-oxo-2,3,9,9a-tetrahydro-1H-fluoren-7:yl)oxy]acetate, 2.5 g.

EXAMPLE 7

-2[(5,6-Dichloro-3-oxo-2,9a-propano-2,3,9,9a-tetrahydro-1H-fluoren-7-yl)oxy]ethanimidamide hydrochloride

Step A

[(5,6-Dichloro-3-oxo-2,9a-propano-2,3,9,9a-tetrahydro-1H-fluoren-7-yl)oxy]acetamide

[(5,6-Dichloro-3-oxo-2,9a-propano-2,3,9,9a-tetrahydro-1H-fluoren-7yl)oxy]acetic acid (3.67 g, 10 mMole) is dissolved in tetrahydrofuran (30 ml) and 1,1-carbonyldiimidazole (1.78 g, 11 mMole) and the mixture stirred at ambient temperature for 30 minutes. The solution is saturated with ammonia gas and then stirred at ambient temperature for 24 hours and at 50° for 16 hours. Evaporation of the solvent and addition of water yields [(5,6-dichloro-3-oxo-2,9a-propano-2,3,9,9a-tetrahydro-1H-fluoren-7-yl)oxy]acetamide which is separated by filtration, washed with water, and dried.

Step B

[(5,6-Dichloro-3-oxo-2,9a-propano-2,3,9,9a-tetrahydro-1H-fluoren-7-yl)oxy]acetonitrile

[(5,6-Dichloro-3-oxo-2,9a-propano-2,3,9,9a-tetrahydro-1H-fluoren-7-yl)oxy]acetamide (3.65 g, 10 mMole) is dissolved in pyridine (25 ml) and N,N'-dicyclohexylcarbodiimide (2.17 g, 10.5 mMole) in pyridine (15 ml) is added portionwise over 30 minutes with stirring at 15°–20° C. The mixture is then stirred at ambient temperature for 3 hours. The precipitated dicyclohexylurea is removed by filtration and the pyridine removed from the filtrate by evaporation in vacuo. Addition of water to the residue gives the product which is dissolved in methylene chloride, dried over MgSO₄ and the solvent removed to provide the [(5,6-dichloro-3-oxo-2,9a-propano-2,3,9,9a-tetrahydro-1H-fluoren-7-yl)oxy]acetonitrile.

Step C

2-[(5,6-Dichloro-3-oxo-2,9a-propano-2,3,9,9a-tetrahydro-1H-fluoren-7-yl)oxy]ethanimidamide hydrochloride

[(5,6-Dichloro-3-oxo-2,9a-propano-2,3,9,9a-tetrahydro-1H-fluoren-7-yl)oxy]acetonitrile (3.49 g, 10mMole) chloroform (40 ml) and ethanol (650 mg, 11 mMole) are united and saturated with hydrogen chloride gas at 0° C. The mixture is stirred for 16 hours and then basified with 10 normal sodium hydroxide solution. The chloroform layer is separated, washed with water, dried over $K_2CO_3$, and evaporated in vacuo. The residue is dissolved in ethanol (30 ml) and water (5 ml) added. The mixture is stirred and treated with ammonium chloride (700 mg, 12 mMole). After stirring at ambient temperature for 4 hours, the mixture is filtered, the filtrate evaporated to near dryness in vacuo, and the residue treated with acetone (50 ml). The solid that separates is removed by filtration, washed with acetone, dried, and recrystallized from a mixture of ethanol and ether to give 2-[(5,6-dichloro-3-oxo-2,9a-propano-2,3,9,9a-tetrahydro-1H-fluoren-7-yl)-oxy]ethanimidamide hydrochloride.

By usingthe (+) enantiomer of [(5,6-dichloro-3-oxo-2,9a-propano-2,3,9,9a-tetrahydro-1H-fluoren-7-yl)oxy]acetic acid in Example 7, Step A, instead of the racemate and using the product of that reactionin Step B and the product of Step B in Step B, there is obtained the (+)-enantiomer of 2-[(5,6-dichloro-3-oxo-2,9a-propano-2,3,9,9a-tetrahydro-1H-fluoren-7-yl)oxy]ethanimidamide hydrochloride.

Similarly if the (−)-enantiomer is used in Example 7, Step A, the final product in Step C is the (−) enantiomer of 2-[(5,6-dichloro-3-oxo-2,9a-propano-2,3,9,9a-tetrahydro-1H-fluoren-7-yl)oxy]ethanimidamide hydrochloride.

EXAMPLE 8

2-[(5,6-Dichloro-2,9a-ethano-3-oxo-2,3,9,9a-tetrahydro-1-H-fluoren-7-yl)oxy]ethanimidamide hydrochloride By carrying out the reactions as described in Example 7, except that for the [(5,6-dichloro-3-oxo-2,9a-propano-2,3,9,9a-tetrahydro-1H-fluoren-7-yl)oxy]acetic acid used in Example 7, Step A, there is substituted an equimolar amount of [(5,6-dichloro-2,9a-ethano-3-oxo-2,3,9,9a-tetrahydro-1H-fluoren-7-yl)-oxy]acetic acid. There is obtained in Step A [(5,6-dichloro-2,9a-ethano-3-oxo-2,3,9,9a-tetrahydro-1H-fluoren-7-yl)oxy]acetamide.

Using the product of Step A in Step B, there is obtained 2-[(5,6-dichloro-2,9a-ethano-3-oxo-2,3,9,9a-tetrahydro-1H-fluoren-7-yl)oxy]acetonitrile.

Using the product of Step B in Step C, there is obtained 2-[(5,6-dichloro-2,9a-ethano-3-oxo-2,3,9,9a-tetrahydro-1H-fluoren-7-yl)oxy]ethanimidamide hydrochloride.

By using the (+)-enantiomer of the starting material in Example 8, Step A, there is obtained the (+)-enantiomer of 2-[(5,6-dichloro-2,9a-ethano-3-oxo-2,3,9,9a-tetrahydro-1H-fluoren-7-yl)oxy]ethanimidamidehydrochloride in Step C.

Likewise, by using the (−)-enantiomer of the starting material in Example 8, Step A, there is obtained the (−)-enantiomer of 2-[(5,6-dichloro-2,9a-ethano-3-oxo-2,3,9,9a-tetrahydro-1H-fluoren-7-yl)oxy]ethanimidamide hydrochloride in Step C.

EXAMPLE 9

N-Methyl-2-[(5,6-dichloro-3-oxo-2,9a-propano-2,3,9,9-tetrahydro-1H-fluoren-7-yl)oxy]ethanimidamide hydrochloride By conducting the reaction as described for Example 7, Step C, except that the ammonium chloride is replaced by an equimolar amount of methylamine hydrochloride, there is obtained N-methyl-2-[(5,6-dichloro-3-oxo-2,9a-propano-2,3,9,9a-tetrahydro-1H-fluoren-7-yl)oxy]ethanimidamide hydrochloride.

EXAMPLE 10

N,N-Dimethyl-2-[(5,6-dichloro-3-oxo-2,9a-propano-2,3,9,9a-tetrahydro-1H-fluoren-7-yl)oxy]ethanimidamideh ydrochloride By conducting the reaction as described for Example 7, Step C, except that the ammonium chloride is replaced by an equimolar quantity of dimethylamine hydrochloride, there is obtained N,N-dimethyl-2-[(5,6-dichloro-3-oxo-2,9a-propano-2,3,9,9a-tetrahydro-1H-fluoren-7-yl)oxy]ethanimidamide hydrochloride.

EXAMPLE 11

Parenteral solution of the sodium salt of [(5,6-dichloro-3-oxo-2,9a-propano-2,3,9,9a-tetrahydro-1H-fluoren-7-yl)oxy]acetic acid The [(5,6-dichloro-3-oxo-2,9a-propano-2,3,9,9a-tetrahydro-1H-fluoren-7-yl)oxy]acetic acid (Example 2, Step H) (500 mg) is dissolved by stirring and warming with a solution of 0.25N sodium bicarbonate (5.6 ml). The solution is diluted to 10 ml with water and sterilized by filtration. All the water that is used in the preparation is pyrogen-free. The concentration of the active ingredient (calculated as free acid) in the final solution is 5%.

EXAMPLE 12

Parenteral solution of the Sodium Salt of [(5,6-dichloro-2,9a-ethano-3-oxo-2,3,9,9a-tetrahydro-1H-fluoren-7-yl)oxy]acetic acid The [(5,6-dichloro-2,9a-ethano-3-oxo-2,3,9,9a-tetrahydro-1H-fluoren-7-yl)oxy]acetic acid (Example 4, Step J) (500 mg) is dissolved by stirring and warming with a solution of 0.25N sodium bicarbonate (5.8 ml). The solution is diluted to 10 ml with water and sterilized by filtration. All the water that is used in the preparation is pyrogen-free. The concentration of the active ingredient (calculated as free acid) in the final solution is 5%.

Similar parenteral solutions can be prepared by replacing the active ingredient of this Example by any of the other carboxylic acid compounds of this invention.

EXAMPLE 13

Parenteral solution of 2-[(5,6-dichloro-3-oxo-2,9a-propano-2,3,9,9a-tetrahydro-1H-fluoren-7-yl)oxy]ethanimidamide hydrochloride The 2-[(5,6-dichloro-3-oxo-2,9a-propano-2,3,9,9a-tetrahydro-1H-fluoren-7-yl)oxy]ethanimidamide hydrochloride (Example 7, Step C) (547 mg) is dissolved by stirring and warming with water (6 ml). The solution is diluted to 10 ml with water and sterilized by filtration. All the water that is used in the preparation is pyrogen-free. The concentration of the active ingredient (calculated as free base) in the final solution is 5%.

EXAMPLE 14

Parenteral solution of the 2-[(5,6-dichloro-2,9a-ethano-3-oxo-2,3,9,9a-tetrahydro-1H-fluoren-7-yl)oxy]ethanimidamide hydrochloride The 2-[(5,6-dichloro-2,9a-ethano-3-oxo-2,3,9,9a-tetrahydro-1H-fluoren-7-yl)oxy]ethanimidamide hydrochloride (Example 8, Step C) (548 mg) is dissolved by stirring and warming with water (6 ml). The solution is diluted to 10 ml with water and sterilized by filtration. All the water that is used in the preparation is pyrogen-free. The concentration of the active ingredient (calculated as free base) in the final solution is 5%.

Similar parenteral solutions can be preprared by replacing the active ingredient of this Example by any of the other of the imidamide hydrochloride salts of this invention.

EXAMPLE 15

Dry-Filled Capsules Containing 100 mg of Active Ingredient (free base) Per Capsule

|  | Per Capsule |
|---|---|
| [(5,6-Dichloro-3-oxo-2,9a-propano-2,3,9,9a-tetrahydro-1H—fluoren-7-yl)oxy]acetic acid | 100 mg |
| Lactose | 99 mg |
| Magnesium Stearate | 1 mg |
| Capsule (Size No. 1) | 200 mg |

The [(5,6-dichloro-3-oxo-2,9a-propano-2,3,9,9a-tetrahydro-1H-fluoren-7-yl)oxy]acetic acid (Example 2, Step H) is reduced to a No. 60 powder and then the lactose and magnesium stearate are passed through a No. 60 bolting cloth onto the powder and the combined ingredients admixed for 10 minutes and then filled into a No. 1 dry gelatin capsule.

Similar capsules can be prepared by replacing the active ingredient of this Example by any of the other compounds of this invention.

EXAMPLE 16

Dry-Filled Capsules Containing 100 mg of Active Ingredient (free base) Per Capsule

|  | Per Capsule |
|---|---|
| 2-[(5,6-Dichloro-2,9a-ethano-3-oxo-2,3,9,9a-tetrahydro-1H—fluoren-7-yl)oxy]ethanimidamide hydrochloride | 109.6 mg |
| Lactose | 89.4 mg |
| Magnesium Stearate | 1 mg |
| Capsule (Size No. 1) | 200.0 mg |

The 2-[(5,6-dichloro-2,9a-ethano-3-oxo-2,3,9,9a-tetrahydro-1H-fluoren-7-yl)oxy]ethanimidamide hydrochloride (Example 8, Step C) is reduced to a No. 60 powder and then the lactose and magnesium stearate are passed through a No. 60 bolting cloth onto the powder and the combined ingredients admixed for 10 minutes and then filled into a No. 1 dry gelatin capsule.

Similar capsules can be prepared by replacing the active ingredient of this Example by any of the other compounds of this invention.

What is claimed is:

1. A compound of the formula:

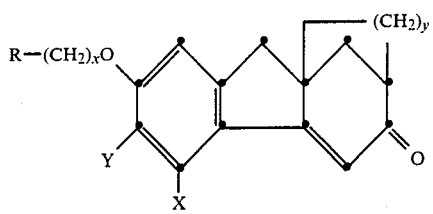

wherein:
R is —COOR$^1$,

$R^1$ is hydrogen, $C_1$–$C_6$ alkyl, $C_1$–$C_6$ alkylcarboxy;
$R^2$ is $NH_2$, $NHR^4$ or $NR^4R^5$;
$R^3$ is NH or $NR^4$;
$R^4$, $R^5$ are each independently lower alkyl, branched or unbranched, containing from 1 to 5 carbon atoms, or amino, provided that $R^4$ and $R^5$ are not both amino;
wherein $R^2$ and $R^3$ may be joined together via $R^4$ to form a heterocyclic ring of 5 or 6 atoms containing 2 nitrogen atoms and 3 or 4 carbon atoms,

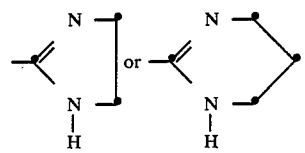

or wherein $R^4$ and $R^5$ may be joined together to form a 5- or 6-membered ring containing one nitrogen atom and 4 or 5 carbon atoms,

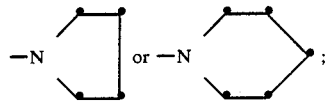

X and Y are halo or lower alkyl, such as methyl; and x is 1 to 4; y is 1 to 3

2. A compound of the formula:

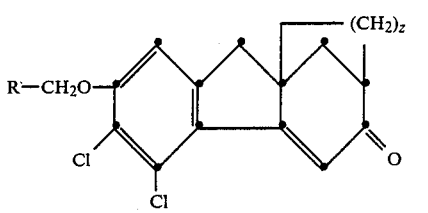

wherein:
R is —COOH,

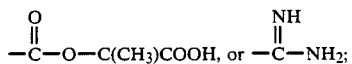

and z is 1 or 2.

3. A compound of claim 1, which is [(5,6-dichloro-3-oxo-2,9a-propano-2,3,9,9a-tetrahydro-1H-fluoren-7-yl)oxy]acetic acid.

4. A compound of claim 3, which is the (+) enantiomer.

5. A compound of claim 3, which is the (−) enantiomer.

6. A compound of claim 1, which is [(5,6-dichloro-2,9a-ethano-3-oxo-2,3,9,9a-tetrahydro-1H-fluoren-7-yl)oxy]acetic acid.

7. A compound of claim 6, which is the (+) enantiomer.

8. A compond of claim 6, which is the (−) enantiomer.

9. A compound of claim 1, which is 2-[(5,6-dichloro-3-oxo-2,9a-propano-2,3,9,9a-tetrahydro-1H-fluoren-7-yl)oxy]ethanimidamide hydrochloride.

10. A compound of claim 9, which is the (+) enantiomer.

11. A compound of claim 9, which is the (−) enantiomer.

12. A compound of claim 1, which is 2-[(5,6-dichloro-2,9a-ethano-3-oxo-2,3,9,9a-tetrahydro-1H-fluoren-7-yl)oxy]ethanimidamide hydrochloride.

13. A compound of claim 12, which is the (+) enantiomer.

14. A compound of claim 12, which is the (−) enantiomer.

15. A compound of claim 1, which is 1-carboxy-1-methylethyl[(5,6-dichloro-2,9a-ethano-3-oxo-2,3,9,9a-tetrahydro-1H-fluoren-7-yl)oxy]acetate.

16. A compound of claim 15, which is the (+) enantiomer.

17. A compound of claim 15, which is the (−) enatiomer.

18. A pharmaceutical composition useful in the treatment of brain injury comprising a pharmaceutical carrier and an effective amount of a compound of claim 1.

19. A method of treating a person with brain injury which comprises administering to such a person an effective amount of a compound of claim 1.

* * * * *